(12) United States Patent
Janigro et al.

(10) Patent No.: US 7,144,708 B2
(45) Date of Patent: Dec. 5, 2006

(54) MARKERS OF BLOOD BARRIER DISRUPTION AND METHODS OF USING SAME

(75) Inventors: Damir Janigro, Cleveland Heights, OH (US); Nicola Marchi, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 407 days.

(21) Appl. No.: 10/462,222

(22) Filed: Jun. 12, 2003

(65) Prior Publication Data

US 2004/0009581 A1    Jan. 15, 2004

Related U.S. Application Data

(63) Continuation-in-part of application No. 09/891,023, filed on Jun. 25, 2001, now Pat. No. 6,884,591.

(60) Provisional application No. 60/388,371, filed on Jun. 12, 2002.

(51) Int. Cl.
*G01N 33/53*    (2006.01)
*G01N 33/567*   (2006.01)

(52) U.S. Cl. ...................... 435/7.1; 435/7.21; 435/7.94

(58) Field of Classification Search ..................... None
See application file for complete search history.

(56) References Cited

U.S. PATENT DOCUMENTS

| | | | |
|---|---|---|---|
| 5,304,367 A | 4/1994 | Biegon | |
| 5,866,347 A | 2/1999 | Swedo et al. | |
| 6,117,989 A | 9/2000 | Bandman et al. | |
| 6,268,223 B1 | 7/2001 | Cornell-Bell et al. | |

OTHER PUBLICATIONS

Power et al. Evolution of the Thyroid Hormone-Binding Protein, Transthyretin. Gen. Comp. Endocrinol. 119: 241-255, 2000.*
Tumor Markers in Peripheral Blood of Patients with Malignant Melanoma: Multimarker RT-PCR Versus a Luminoimmunometric Assay for S-100; Berking, Carola et al.; Arch Dermatol Res (1999) 291: 479-484.
Evaluation of Serum Markers of Neuronal Damage Following Severe Hypoglycaemia in Adults with Insulin-Treated Diabetes Mellitus; Strachan, Mark, W., et al.; Diabetes/Metabolism Research & Reviews 1999; 15: 5-12.
Outwitting the Blood-Brain Barrier for Therapeutic Purposes: Osmotic Opening and Other Means; Kroll, Robert A. & Neuwelt, Edward A.; Neurosurgery, vol. 42, No. 5; May 1998.
Autoantibodies in Neurodegenerative Diseases: Antigen-Specific Frequencies and Intrathecal Analysis; Terryberry, J.W., et al.; Neurobiology of Aging, vol. 19, No. 3, pp. 205-216, 1998.
Cerebrospinal Fluid Analysis Differentiates Between Relapsing-Remitting and Secondary Progressive Multiple Sclerosis; Jongen, Peter J. H. et al.; Neurol Neurosurg Psychiatry 1997; 63: 446-451.

S-100 Release in Hypothermic Circulatory Arrest and Coronary Artery Surgery; Wong, Carl H. et al.; Ann Thorac Surg 1999; 67: 1911-4.
Serum S100 Protein: A Potential Marker for Cerebral Events During Cardiopulmonary Bypass; Westaby, Stephen et al.; Ann Thorac Surg 1996; 61: 88-92.
Serum anti-GFAP and anti-S100 autoantibodies in brain aging, Alzheimer's disease and vascular dementia; Mecocci, P. et al.; Journal of Neuroimmunology 57 (1995) 165-170.
Uncontrolled Reoxygenation by Initiating Cardiopulmonary bypass is Associated with Higher Protein S-100 in Cyanotic Versus Acyanotic Patients; Matheis, G. et al.; Thorac Cardiov Surg 2000; 48: 263-268.
Missler et al. (Jul. 1, 2000) "Validation and Comparison of Two Solid-Phase Immunoassays for the Quantification of S-100b in Human Blood." Clinical Chemistry 46(7): 993-996.
Takahashi et al. (Aug. 1, 1999) "Rapid and Sensitive Immunoassay for the Measurement of Serum S100b Using Isoform-specific Monoclonal Antibody." Clinical Chemistry 45(8): 1307-1311.
Herrmann et al. (2000) "Release of Glial Tissue-Specific Proteins After Acute Stroke." Stroke 31: 2670-2677.
Marchi et al. (2003) "Serum Transthyretin Monomer as a Possible Marker of Blood-to-CSF Barrier Disruption." The Jour. of Neuroscience 23(5):1949-1955.
Bonfrer, JM, Korse, CM<Nieweg, OE, Rankin, EM (1998) The luminescence immunoassay S-100: a sensitive test to measure ciculating S-100B: its prognostic value in malignant melanoma. Br J Cancer 77: 2210-2214.
Borchez L, Naeyaert JM (2000) Serological markers for melanoma, Br J Dermatol 143: 256-268.

(Continued)

*Primary Examiner*—Janet L. Andres
*Assistant Examiner*—Gregory S Emch
(74) *Attorney, Agent, or Firm*—Hamilton, Brook, Smith & Reynolds, P.C.

(57) ABSTRACT

The present invention relates generally to a peripheral marker or markers of blood barrier integrity and methods of using same in the diagnosis, prognosis, and treatment of a variety of diseases. The peripheral marker(s) of the present invention are particularly useful in the differential diagnosis of diseased states. The preferred embodiments of the present invention relate to methods, compositions, kits, and assays useful in determining the integrity or permeability of either a blood CSF barrier or a blood brain barrier. The various embodiments of the present invention can be used to identify subjects at risk for developing a disease associated with increased permeability of the blood brain barrier, as well as to provide insight on the ability of an agent or agents to pass through the blood brain barrier. Embodiments of the present invention preferably involve the use of subject derived blood samples to determine the occurrence and level of circulating proteins indicative of blood brain barrier permeability or integrity. The embodiments of the present invention also provides screening methods for diagnosis, prognosis, susceptibility, or degree of permeability of penetration of the blood brain barrier by detecting the presence of serum Transthyretin either directly or through the use of antibodies.

10 Claims, 4 Drawing Sheets

OTHER PUBLICATIONS

Buccoliero AM, Caldarella A, Noccioli B, Fiorini P, Taddei A, Taddei GL (2002) Brain hetertopia in pharyngeal region. A morphological and immunohistochemical study. Pathol Res Pract 198: 59-63.

Chakrabarty A, Franks AJ (1999) Meningioangiogmatosis: a case report and review of the litaterature. Br J Neurosurg 13: 167-173.

Crossen JR, Goldman DL, Dahlborg SA, Neuwelt EA (1992) Neuropsychological assessment outcomes of nonacquired immunodeficiency syndrome patients with primary central nervous system lymphoma before and after blood-brain barrier disruption chemotheraphy. Neurosurgery 30: 23-29.

Davidsson P, Paulson L, Hesse C, Blennow K, Nilsson CL (2001) Proteome studies of human cerebrospinal fluid and brain tissue using a preparative two-dimensional electrophoresis approach prior to mass spectrometry. Proteomics 1: 444-452.

Davson H, Segal MB (1995) The proteins and other macromolecules of the CSF, In: Physiology of the CSF and of the blood-brain barrier (Davson H, Segal MB, eds), pp. 573-606. New York, NY: CRC.

Dyck RH, Van Eldik LJ, Cynader MS (1993) Immunohistochemical localization of the S-100 beta protein in postnatal cat visual cortex: spatial and temporal patterns of expression in cortical and subcortical glia. Brian Res Dev Brain Res 72: 181-192.

Feany MB, Anthony DC, Fletcher CD (1998) Nerve sheath tumours with hybrid features of neurofibroma and schwannoma: a conceptual challenge. Histopathology 32: 405-410.

Grocott HP, Arrowsmith JE (2001) Serum S100 protein as a marker of cerebral damage during cardiac surgery. Br J Anaesth 86: 289-290.

Grocott HP, Laskowitz DT, Newman MF (2001) Markers of cerebral injury. In: The brain and cardiac surgery (Newman. SP, Harrison MJG, eds), pp. 113-142. Amsterdam, NL: Harwood Academic Publishers.

Hamilton JA, Benson MD (2001) Transthyretin: a review from a structural perspective. Cell Mol Life Sci 58: 1491-1521.

Herbert J, Wilcox JN, Pham KT, Fremeau RT, Jr., Zeviani M, Dwork A. Soprano DR, Makover A, Goodman DS, Zimmerman EA,. (1986) Transthyretin: a choroids plexus-specific transport protein in human brain. The 1986 S. Weir Mitchell award. Neurology 36: 900-911.

Hiraoka A, Tominaga I, Hori K (2000) Sodium dodecylsulfate capillary gel electrophoretic measurement of the concentration ratios of albumin and alpha2-macroglobulin in cerebrospinal fluid and serum of patients with neurological disorders. J Chromatogr A 895: 339-344.

Hund E, Linke RP, Willig F, Grau A (2001) Transthyretin-associated neuropathic amyloidosis. Pathogenesis and treatment. Neurology 56: 431-435.

Ingebrigsten T, Romner B, Marup-Jensen S, Dons M, Lundqvist C, Bellner J, Alling C, Borgesen SE (2000) The clinical value of serum S-100 protein measurements in minor head injury: a Scandinavian multicentre study. Brain Inj 14: 1047-1055.

Ingebrigtsen T, Waterloo K, Jacobsen EA, Langbakk B, Romner B (1999) Traumatic brain damage in minor head injury: relation of serum S-100 protein measurements to magnetic resonance imaging and neurobehavioral outcome. Neurosurgery 45: 468-475.

Janigro, D., Fazio, V., Cucullo, L., and Marchi, N. Markers of BBB damage and inflammatory processes. Soc.for Neuroscience Annual Meeting 580.9 2002.

Jonsson H. Johnsson P, Alling C, Westaby S, Blomquist S (1998) Significance of serum S100 release after coronary artery bypass grafting. Ann Thorac Surg 65: 1639-1644.

Kapural M, Bengez L, Barnett G, Perl J, II, Masaryk TJ, Apollo D, Mayberg MR, Janigro D (2002) S-100B as a possible serum marker for disruption on the blood-brain barrier. Brain Res 940: 102-104.

Mercier F, Hatton GI (2000) Immunocytochemical basis for a meningeo-glial network. J Comp Neurol 420: 445-465.

Molloy MP (2000) Two-dimensional electrophoresis of membrane proteins using immobilized pH gradients. Anal Biochem 280: 1-10.

Monaco HL (2000) The transthyretin-retinol-binding protein complex. Biochim Biophys Acta 1482: 65-72.

Mrak RE, Flanigan S, Collins CL (1994) Malignant acoustic Schwannoma. Arch Pathol Lab Med 118: 557-561.

Neuwelt EA, Frenkel EP, Diehl J, Vu LH, Rapoport SI, Hill SA (1980) Reversible osmotic blood-brain barrier disruption in humans: implications for the chemotherapy of brain tumors. Neurosurgery 7: 44-52.

Neuwelt EA, Goldman DL, Dahlborg SA, Crossen J, Ramsey F, Roman Goldstein S, Braziel R, Dana B (1991) Primary CNS lymphoma treated with osmotic blood-brain barrier disruption: prolonged survival and preservation of cognitive function. J Clin Oncol 9: 1580-1590.

Puchades M, Westman A, Blennow K, Davidsson P (1999) Analysis of intact proteins from cerebrospinal fluid by matrix-assisted laser desorption-ionization mass spectrometry after two-dimensional liquid-phase electrophoresis. Rapid Commun Mass Spectrom 13: 2450-2455.

Reiber H (1998) Cerebrospinal fluid—physiology, analysis and interpretation of protein patterns for diagnosis of neurological diseases. Mult Scler 4: 99-107.

Reiber H (2001) Dynamics of brain-derived proteins in cerebrospinal fluid. Clin Chim Acta 310: 173-186.

Reiber H, Peter JB (2001) Cerebrospinal fluid analysis: disease-related data patterns and evaluation programs. J Neurol Sci 184: 101-122.

Roman-Goldstein S, Mitchell P, Crossen JR, Williams PC, Tindall A, Neuwelt EA (1995) MR and cognitive testing of patients undergoing osmotic blood-brain barrier disruption with intraarterial chemotherapy. AJNR Am J Neuroradiol 16: 543-553.

Ross JS, Masaryk TJ, Modic MT (1989) Three-dimensional FLASH imaging: applications with gadolinium-DTPA. J Comput Assist Tomogr 13: 547-552.

Saraiva MJ (2001) Transthyretin mutations in hyperthyroxinemia and amyloid diseases. Hum Mutat 17: 493-503.

Schussler GC (2000) The thyroxine-binding proteins. Thyroid 10: 141-149.

Segal MB (2000) The choroid plexuses and the barriers between the blood and the cerebrospinal fluid. Cell Mol Neurobiol 20: 183-196.

Stanness KA, Guatteo E, Janigro D (1996) A dynamic model of the blood-brain barrier "in vitro". Neurotoxicology 17: 481-496.

Stanness KA, Westrum LE, Mascagni P, Fornaciari E, Nelson JA, Stenglein SG, Janigro D (1997) Morphological and functional characterization of an *in vitro* blood-brain barrier model. Brain Res 771: 329-342.

Glasner, H. *Barrier impairment and immune reaction in the cerebrospinal fluid*, Eur. Neurol. 1975, vol. 13, No. 4, pp. 304-314.

Adinolfi, M. et al., *Levels of plasma protein in human and rat fetal CSF and the development of the blood-CSF barrier*, Neuropadiatrie, Nov. 1977, vol. 8, No. 4, pp. 345-353.

Takeoka, T. et al., *Impairment of blood-cerebrospinal fluid barrier in multiple sclerosis*, Journal of Neurochemistry, Oct. 1983, vol. 41, No. 4, pp. 1102-1108.

Cheng, L.Y. et al., *Film autoradiography identifies unique features of [125I]3,3'5'-(reverse) triiodothyronine transport from blood to brain*, Journal of Neurophysiology Jul. 1994, vol. 72, No. 1, pp. 380-391.

Marchi, N. et al., *Serum transthyretin monomer as a possible marker of blood-to-CSF barrier disruption*, Journal of Neuroscience, Mar. 1, 2004, vol. 23, No. 5, pp. 1949-1955.

Larsen, P.D et al., *Cerebrospinal fluid Transthyretin in the Neonate and Blood-Cerbrospinal Fluid Barrier Permeability*, Ann Neurol, Jun. 1989, vol. 25, No. 6, pp. 628-630.

\* cited by examiner

MARKERS OF BLOOD BARRIER DISRUPTION AND METHODS OF USING SAME

PRIORITY

This application claims priority from U.S. Provisional Application Ser. No. 60/388,371 filed Jun. 12, 2002 the contents of which are incorporated herein by reference in their entirety. This application is a continuation-in-part of U.S. Ser. No. 09/891,023, now U.S. Pat. No. 6,884,591, filed Jun. 25, 2001, entitled Peripheral Marker of Blood Brain Barrier Permeability

GOVERNMENT INTEREST

The United States Government may have certain interests under Grant Nos. NIH-NS43281, NIH-HL51614, NIH-NS38195 as this work was supported in part by the National Institutes of Health (NIH-NS43281, NIH-HL51614, NIH-NS38195).

BACKGROUND OF THE INVENTION

The blood brain barrier and blood cerebrospinal fluid barriers prevent many compounds in the blood stream from entering the tissues and fluids of the brain and central nervous system ("CNS"). It is generally recognized that nature provides these barriers to ensure a toxin free environment for neurologic function. The blood brain barrier ("BBB") is of great importance for the maintenance of a constant environment for optimal neurological function. Most metabolic substrates (i.e. sugars and amino acids) are hydrophilic, and traverse these barriers only by specific carrier-mediated transport systems. Other molecules traverse the barriers more freely.

Loss of blood-brain barrier (BBB) function is an etiologic component of many neurological diseases. An intact BBB may restrict the delivery of certain therapeutic substances to the brain. Thus, measuring BBB function can be important to diagnosing disease progression and monitoring time-dependent changes in BBB integrity when chemotherapic penetration may be enhanced. At present, invasive and expensive techniques such as contrast-enhanced magnetic resonance imaging, CT scan and lumbar puncture are utilized to clinically assess BBB integrity.

Both sites of cerebrospinal fluid ("CSF") formation, the choroid plexus as well as blood brain barrier endothelial cells, allow negligible passage of protein. Macromolecules such as polypeptides/protein, can cross an endothelial cell barrier primarily in three ways: between the cells through cell-cell junctions (paracellular pathway), through the EC, via pores (fused vesicles), or transcellularly via shuttling specific vesicles and receptors. Electron microscopic evidence suggests that macromolecules are shuttled across the endothelial barrier via vesicles.

BBB assessment by imaging or cerebrospinal fluid sampling is based on direct or indirect determination of protein permeability across the BBB. CNS proteins are normally asymmetrically distributed, with generally much high concentration in plasma than in CSF. Thus, the appearance of plasma proteins in cerebrospinal fluid ("CSF") is a hallmark of numerous CNS disorders with presumed or overt BBB disruption. Only a few proteins are synthesized exclusively by, or are present in higher concentrations in CSF or interstitial compartment compared to the blood.

Samples of CSF can be intra surgically taken from the ventricles or from the sub-arachnoid space in the brain. An obvious limitation of intrathecal detection of blood brain-barrier intactness resides in the fact that sampling of CSF is invasive, and that the sample itself may be contaminated by the procedure. In addition, it has been known for a long time that a gradient in protein content exists from the brain to the lumbar cord. In fact, the concentrations of protein in segments distal to the site of CSF reduction (ventricles) are known to be much higher. It appears that, at least in part, the increased protein in the lumbar compartment of the CSF is due to a combination of protein secreted by parenchymal cells plus a small amount of protein leakage across the blood brain-barrier.

Ongoing or incipient systemic dysfunction of the heart, pancreas, liver or kidney can often be detected with the help of biochemical markers, whose specificity and known kinetics permit diagnostic and prognostic evaluation. The complexity of CNS function and the multiple kinetic parameters involved in bio-distribution across the blood brain barrier and within the brain parenchyma imposes a considerable burden for the interpretation of putative biochemical markers present in serum or cerebrospinal fluid. While changes in the composition of cerebrospinal fluid are commonly used to diagnose a variety of neurological diseases, the invasiveness of the procedures involved greatly diminishes their usefulness.

SUMMARY OF THE INVENTION

The present invention is directed to a peripheral marker, used alone or in combination with other markers, which is indicative of the permeability of the blood brain barrier ("BBB") or blood cerebrospinal fluid barrier ("BCSFB"). and the blood cerebrospinal fluid barrier as BCSFB. The term blood barrier may be used herein to refer to and include both BBB and BCSFB.

The present invention is based on monitoring or measuring a marker or markers of BBB and/or BCSFB permeability, particularly transthyretin TTR alone or in combination with other markers of neuronal disease or damage (e.g. S-100β). S-100β is primarily synthesized in the brain by the end feet process of the astrocytes and is quickly released from the brain in the blood when the BBB is disrupted. S-100β has also been found in other tissues but at lower concentrations. Although the appearance of S-100β in plasma correlates well with BBB openings, S-100β has been shown to increase in plasma, CSF or both as a consequence of other pathologies not limited to the CNS. S-100β may detect brain damage or indicate advanced metastasis in melanoma patients. Transthyretin is a reliable marker of permeability of the BCSFB. Preferably, levels of TTR are determined and compared with a control sample (e.g., levels found in a normal population); changes above these baseline values being indicative of blood brain barrier dysfunction or permeability. Both the amount and form of the TTR protein may be used. TTR protein may also be observed as an indicator of brain damage, along with other markers of neuronal distress.

The embodiments of the present invention provide: methods; compositions; and kits for the diagnostic and prognostic evaluation of permeability of the BCSFB and/or the BBB. Additionally, certain embodiments of the present invention may be utilized to identify compromise of the blood-CSF barrier rather than the blood brain barrier and vice-versa. These embodiments are particularly useful in the identification of subjects possessing a predisposition to passing or preventing agents from passing the BCSFB or BBB, and for monitoring patients undergoing treatment involving the integrity of the BCSFB or BBB, based on the detection of increased levels of TTR protein expression in a blood derived sample of subjects alone or in combination with other neuronal markers.

In one embodiment, the present invention provides for a method for diagnosis of blood barrier permeability by means of detecting levels of TTR protein in a sample of biological fluid, preferably a blood sample. Additionally, the method for diagnosis can include detecting the levels of markers of neuronal distress, suitable markers being, for example, NSE and GFAP, and albumin. Furthermore, comparisons can be made with BBB function vis-à-vis the levels of S-100β in the sample. The level of TTR protein detected can be used as a measure of BCSFB permeability. The TTR protein is preferably detected using an immunoassay, such as an immunoprecipitation assay, but can also be detected by bi-dimensional gels or other means of detecting TTR.

Another embodiment of the present invention provides for detecting onset of neuronal distress in a patient by identifying elevated levels of TTR protein in the biological fluid, such as blood or serum. Additionally, the method for detection can include detecting the levels of markers of neuronal distress, combined with alternative methods to measure BBB function (S-100β) alone or in conjunction with suitable markers of neuronal distress including NSE, GFAP and MBP.

Another embodiment of the present invention provides for a method of treating a patient in need thereof with a therapeutic agent. The method includes the steps of administering an agent which opens the BBB or BCSFB and verifying elevated levels of TTR protein in the blood (alone or in combination with other suitable markers). The therapeutic agents that may be employed include chemotherapeutics, pharmaceuticals, neuropharmaceuticals, potential neuropharmaceuticals, and other neurologically active agents.

Another embodiment of the present invention comprises assays developed to detect the level of TTR proteins in a subject's serum sample. Such assays include immunoassays wherein the TTR proteins are detected by their interaction with anti-TTR specific antibodies. For example, TTR antibodies or fragments of antibodies may be used to quantitatively detect the presence of TTR proteins in a serum sample.

The embodiments may also involve the use of the TTR protein antigens in immunoassays designed to detect the presence of serum autoantibodies to the TTR protein antigens. Such immunoassays can be utilized to determine the permeability of the BCSFB and BBB. Moreover, the monitoring of TTR levels can be used prognostically to stage progression of the disease or the treatment.

Another embodiment of the present invention provides for a kit for diagnosis and prognosis of blood barrier integrity in a subject. The kit includes a component for detecting a peripheral marker of blood barrier integrity. The component is utilized for the purpose of detecting the presence of TTR protein in a blood sample, where elevated levels of TTR protein is indicative of blood barrier opening. The kit may also be designed to localize the area of permeability or rule out disruption of a particular portion of the blood barrier (e.g. BBB disruption).

Another embodiment of the present invention provides for pre-packaged diagnostic kits, which will be conveniently used in clinical settings, to diagnose or monitor patients with impaired BBB or BCSFB integrity. The kits will also be utilized to monitor the efficacy of compounds used for treatment of diseases associated with BBB or BCSFB integrity or lack thereof.

Also disclosed are possible uses of this observation to predict incipient neurological disease, adverse reactions to medical treatment and efficacy or toxicity of drugs administered systemically.

Additional aspects and applications of the present invention will become apparent to the skilled artisan upon consideration of the detailed description of the invention, which follows.

DETAILED DESCRIPTION OF THE INVENTION

Figure 1:
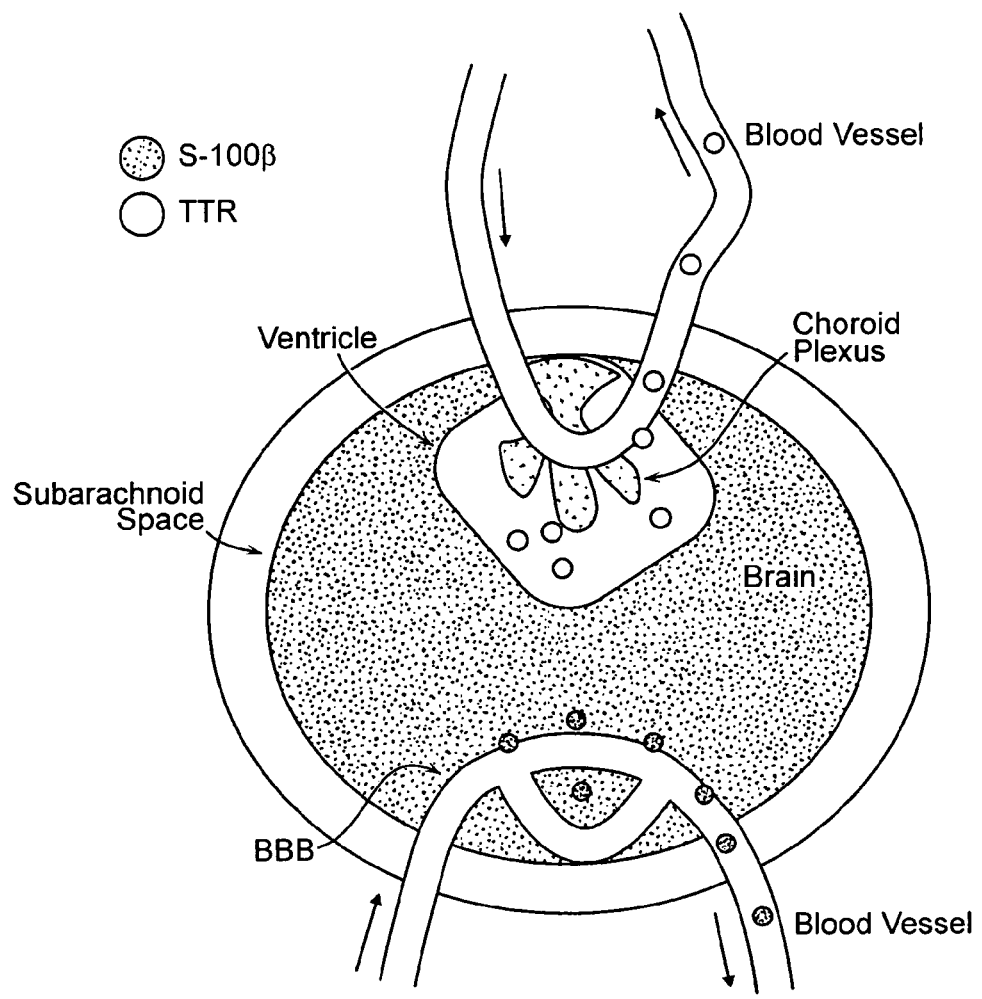
FIG. 1 is a diagrammatic representation of the different distribution between S-100β and TTR in the brain.

Before the various embodiments of the present invention are described, it is to be understood that this invention is not limited to the particular methodology and protocols described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to the "antibody" is a reference to one or more antibodies and equivalents thereof known to those skilled in the art, and so forth.

By "sample" it is meant a volume of fluid or tissue, such as blood or CSF, but preferably blood which is obtained at one point in time. A sample can be as little as 2.5 mL (or less) taken from the subject. Further, as will be discussed in detail below, all the markers can be measured with one assay device or by using a separate assay device for each marker, in which case aliquots of the same fluid sample can be used or different fluid samples can be used. The analyses should be carried out within some short time frame after the sample is taken, e.g., within about one-half hour, so the data can be used to prescribe treatment as quickly as possible.

The terms "above normal" and "above threshold" are used herein to refer to a level of TTR that is greater than the level of TTR observed in normal individuals in a given environment, that is, individuals who are not undergoing an event, i.e. an opening of a blood barrier. These terms contemplate a level that is significantly above the normal level found in individuals. The term "significantly" refers to statistical significance. The assay method by which the analysis for the TTR protein is carried out, must be sufficiently sensitive to be able to detect the level of the marker which is present over the concentration range of interest and also must be highly specific. Ranges of TTR should be detectable from about 0.001 mg/L to about 100 mg/L in blood.

The assay devices used according to the invention can be arranged to provide a semi-quantitative or a quantitative result. The term "semi-quantitative" is meant to reflect the ability to discriminate between a level which is above the elevated marker protein value, and a level which is not above that threshold. The statistical methods used herein generally present data as means±SEM ANOVA was needed to determine significance. Origin 7.0 (Microcal) was used for statistical analysis.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference. Nothing herein is to be construed as an admission that the invention is not entitled to antedate such disclosure by virtue of prior invention.

The barrier that separates the blood from the cerebral interstitial fluid is defined as the BBB, while the one that separates the blood and cerebrospinal fluid (BCSFB) discontinues the circulation between the blood and cerebrospinal fluid. Both barriers are formed by cell layers expressing intercellular tight junctions; whereas the BBB is made of endothelial cells, the blood-to-CSF barrier consists of epithelial cells. To a large extent, both CNS barriers are impermeant to macromolecules, thus hampering passage of proteins from the blood to the brain/CSF and vice versa. As a consequence of CSF production by choroid plexus epithelium and the endothelial BBB, CSF protein content is significantly lower than plasma. Thus, when the BBB or the BCSFB are breached, plasma proteins leak into the CSF.

Recent evidence suggests that the opposite phenomenon, i.e., leakage of CSF-specific proteins into blood, may also be used to detect BBB integrity. S-100β is, at least theoretically, an ideal marker of BBB function, since it is heavily expressed by perivascular astrocytes, appears in blood seconds after BBB opening, and it is normally low in serum of control subjects Measurement of BBB intactness by peripheral blood analysis is desirable in a number of pathologies, including stroke, intracerebral hemorrhage and head injury. Similarly, assessment of functionality of the blood-to-CSF barrier may be useful to detect incipient or ongoing brain inflammation, hydrocephalus, etc. Such a marker is currently unavailable.

In chronic neurological diseases (e.g., multiple sclerosis), BBB openings may have both therapeutic and etiologic significance, since a correlation between severity of symptoms and BBB function has been suggested and given the fact that promising therapies based on brain-derived proteins have failed largely because of poor penetration of these protein compounds across the BBB.

Protein profiles from blood samples obtained from patients undergoing iatrogenic BBB disruption (BBBD) with intrarterial hyperosmotic mannitol were compared with pre-BBB opening serum. A low molecular weight protein (14 kDa) identified by mass spectroscopy as transthyretin (TTR) consistently correlated with BBBD. Protein gel electrophoresis and immunodetection confirmed that TTR was indeed extravasated in its monomeric form when CNS barriers were breached. The time course of TTR extravasation was compared with release from the brain of another BBB integrity marker, S-100β (11 kDa). Kinetic analysis revealed that appearance of S-100β, presumably originating from perivascular astrocytic end feet, preceded extravasation of TTR by several minutes. Since TTR is primarily localized in choroid plexus and, as a soluble monomer, in cerebrospinal fluid (CSF), we concluded that while S-100β is a marker of BBB integrity, TTR may be preferentially a peripheral tracer of blood-to-cerebrospinal barrier.

MATERIAL AND METHODS

The Cleveland Clinic Brain Tumor Institute provides a treatment called blood-brain barrier disruption for primary central nervous system lymphomas, primitive neuroectodermal tumors, some gliomas, CNS germinoma and some metastatic brain tumors (such as breast, small cell lung or germ cell). All procedures were performed after informed consent was obtained using protocols approved by the Cleveland Clinic Foundation Institutional Review Board. In this protocol, intrarterial mannitol (1.4 M) is administered via a carotid or vertebral artery, and BBBD is confirmed by CT immediately after chemotherapy.

Sucrose gradient separation was performed to divide proteins by molecular weight. 10 ml of discontinuous 10%–25%–40% gradient and 200 μl of sample (75 μl of serum, 125 μl of gradient buffer) were used. The upper fraction was collected after 16 hours of centrifugation at 4° C. (225,0000×g). The low molecular weight fraction was filtered with a 3 kDa molecular weight cut-off (Amicon Centricon YM 3000) for 6 hours (5800×g) to remove sucrose. Both SDS and NO-SDS-PAGE were used. Non-SDS-PAGE samples were analyzed in non-denaturing condition.

Identification of TTR protein was performed by Western blotting techniques. Serum samples were obtained from the BBBD procedures and protein were probed overnight at 4° C. with primary TTR rabbit anti-human antibody (1:1000; Dako). Protein concentration was estimated according to the Bradford assay method. Relative expressions of proteins were determined by densitometric analysis using Scion Image Software. This approach was used to quantify the TTR and haptoglobin data shown in FIG. 3. Radial Immunodiffusion (RID) was used to quantitatively determine TTR in serum. Prefabricated immunodiffusion plates were purchased from Kent Laboratories, Inc. (Bellingham, Wash.). Experiments were performed as recommended by the vendor.

For mass-spectroscopy a liquid chromatography-mass spectroscopy (LC-MS) system Finnigan LCQ-Deca ion trap mass spectrometer system with a Protana microelectrospray ion source interfaced to a self-packed 10 cm×75 um inner diameter Phenomenex Jupiter C18 reversed-phase capillary chromatography column was used. Data were analyzed by using all collision-induced dissociation spectra collected in the experiment to search the National Center for Biotechnology Information non-redundant database with the search program TurboSequest. All matching spectra were verified by manual interpretation. The interpretation process was also aided by additional searches using the programs Mascot and Fasta, performed as needed.

Transthyretin represents a disproportionate fraction (25%) of CSF protein, prompting the suggestion that it is either selectively transported across the blood-CSF barrier or synthesized de novo within the CNS. It has been demonstrated that the latter is the case and that the epithelial cells of the choroid plexus are the site of synthesis in both rats and humans. TTR shows high-affinity binding to plasma retinol-binding protein and is involved in the transport of tyrosine in to the brain. TTR variants have been implicated in a variety of human disorders, including Alzheimer's dementia.

In the blood, TTR is usually present in its tetrameric form and originates from liver secretion. About 40% of plasma TTR circulates in a tight protein-protein complex with the plasma retinol-binding protein (RBP). TTR is synthesized by choroid plexus epithelial cells, and subsequently released into the CSF. Plasma TTR is present in the homotetramer form, while its CSF form is primarily monomeric. In contrast to the BBB marker S-100β, TTR is not expressed by perivascular astrocytes or any other cells in the brain parenchyma. Although levels of TTR in brain interstitial fluid have not been measured, it is unlikely that selective opening of the BBB (but not of the blood-to-CSF barrier) would cause extravasation of TTR in plasma. FIG. 1 illustrates different distribution between S-100β and TTR in the brain. In the brain, S-100β is synthesized primarily by the astrocytes surrounding the BBB, whereas TTR is synthesized by the choroids plexuses and is found in the ventruicular CSF. This topographic segretation may explain the different roles of these markers.

Although the appearance of S-100β serum occurred immediately after BBBD by mannitol, TTR increases lagged behind. We interpreted this as indirect evidence linking TTR extravasation to blood-to-CSF barrier rather than BBB impairment. This was further supported by the following considerations: S-100β but not TTR is expressed at the BBB; TTR is highly concentrated at the site of the blood-to-CSF barrier and in the ventricular CSF; and, Brain TTR is primarily monomeric, as is the protein we found increased in plasma after BBBD. Alternatively, delayed appearance of TTR may be due to the different spatial concentration gradients acting on S-100β and TTR (different cell sources), and the time taken for TTR to reach the brain capillaries from the CSF. Finally the difference in molecular weight between S-100β (11 kDa) and TTR (14 kDa) may be responsible to some degree for these differences.

Transthyretin, particularly the $TTR_{monomer}$, is a candidate marker for blood-to-CSF barrier dysfunction, in a manner similar to S-100β in its relationship to the BBB proper. Transthyretin has broad utility in the management or diagnosis of disorders such as hydrocephalus, meningitis, and other cerebrovascular disorders.

Understanding the anatomical features and function of the blood brain barrier provides insight into the vast applicability and importance of the present invention. The BBB is a continuous, tight-junctioned, endothelial cell layer. The endothelial layer actually consists of two separate cell membranes, one on the inside of the vessels (luminal) and one on the outside (abluminal) separated by 300–500 nm of thick cytoplasm. The endothelial cells, however, are only one part of a "BBB complex", which consists of astrocytes, pericytes, microglia, and neurons. All of these cell types play a role in the induction and maintenance of the specialized BBB endothelium. The microvascular endothelium shares a common basement membrane with astrocytes and pericytes. Beyond the basement membrane in parenchymal vessels of the brain lies a close investment of end feet from neuroglial cells, predominantly astrocytes. Astrocytes and their processes invest more than 90% of endothelial capillaries and their end feet are projected tightly around the endothelial cells. Therefore, the glial end feet are a natural candidate to mediate a communication link between neurons and capillaries. Recent evidence has shown that shear stress promotes the expression of numerous genes involved in various aspects of endothelial cell function. Indirect evidence suggests that flow is an initial step of endothelial differentiation, suggesting that flow cessation or changes on flow pattern (e.g., as seen during ischemia reperfusion or hypo-hypertension) may impact BBB integrity or tightness. Pericytes also limit transport across the BBB along with macrophages through the ability to phagocytes compounds which have crossed the endothelial barrier and therefore act as a second line of defense just behind of the endothelium. The possibility exists that pericyte-specific proteins may become useful markers of BBB function, owing to their proximity to the plasma compartment and their strategical location of the endothelial-brain interface.

The BBB is not a static organ, and numerous factors affect BBB permeability. In the early 1960s, Majno and Palade showed that after exposure of tissue to histamine, carbon particles injected into the blood compartment entered the parenchyma (tissue) selectively via post capillary venule endothelial cells ("ECs"). Moreover, gaps were occasionally seen. In a subsequent study, Majno et al observed that the nucleus of these ECs had a wrinkled appearance and postulated that contraction of the EC was the basis for the increased extravasation of macromolecules. This insightful observation is supported by more recent findings and constitutes the rationale for "osmotic opening" of the BBB.

A functional barrier in addition to an anatomic barrier, the BBB is of great importance for the maintenance of a constant environment for optimal CNS function. There are marked apical/basal differences in the distribution of carriers and enzymes, which distinguishes the specialized BBB endothelium from peripheral endothelium. By attaching therapeutically active macromolecules to agents that bind these specialized transport systems, the macromolecules may be taken up, transported through the endothelial cells, and ultimately released on the abluminal side of the vessel (brain parenchyma). Owing to the close interaction of perivascular glia and brain capillary endothelial cells, it is commonly accepted that the "blood brain barrier organ" is constituted not only by endothelial cells, but glial end feet as well. Current understanding of the mechanism of neuro-immunological interactions of specialized cells with the blood brain barrier has also suggested involvement of both perivascular pericytes and microglia as active components of the blood brain barrier. Under neuro-pathological conditions, both perivascular astrocytes and blood brain barrier endothelial cells undergo significant changes.

In many diseases that affect the brain, the cerebral endothelium plays an active part in the disease process with the BBB becoming disrupted, or modified, in such a way there is a dramatic increase in vascular permeability. Theoretically, several ways exist in which various molecules can pass the endothelium. These include intercellular routes, vesicular transport, or direct transcellular penetration through damaged endothelium. BBB dysfunction may be a cause or consequence of a particular disease process. Diseases in which increased BBB permeability have been reported include neoplasia, ischemia, hypertension, dementia, epilepsy, infection, multiple sclerosis, and trauma. The effect of a disease on BBB function will secondarily affect the cerebral blood flow and vascular tone in the brain, which further influences transport across the BBB. Besides the effects of increased vascular permeability on the brain parenchyma, a question of great significance is whether, in certain neuropathological conditions, the BBB disturbance constitutes the main pathogenic factor itself, which then triggers a sequence of events molding the final pathological state.

The fact that TTR appears to be being released from the cerebrospinal fluid may explain why its appearance in plasma delayed compared to other markers directly available in the perivascular space. This allows for an embodiment of the present invention, wherein TTR is used to measure BBB permeability or BCSFB permeability. The late appearance would appear to be particularly useful in detecting or diagnosing BBB permeability if this marker is used in conjunction with other fast-released protein such as S-100β.

In its tetrameric form, TTR is in plasma at levels much higher than CSF. According to the considerations listed above, one would expect TTR to behave, in the presence of a leaky BBB as albumin, thus promptly moving from the blood to the brain compartment. However, the CSF contains high levels of the monomeric, low molecular weight form of TTR. It is this form that preferably allows peripheral determinations of BBB intactness in the serum. It may also be possible to detect differential amounts of the tetramer in the blood.

A peripheral marker of blood barrier permeability should include most of the following properties: plasma levels in control subjects must be exceedingly low or undetectable; similarly, under normal conditions CSF levels must be constant or, ideally, low; significant increases of the marker's concentrations must occur at early stages of neuronal distress; CSF changes must be reflected by comparable changes in plasma levels. Of the candidates, TTR monomer would appear to be a suitable peripheral marker in reflecting BBB permeability and/or neuronal damage with regard to those characteristics.

Blood samples from three patients affected by primary brain lymphoma who underwent monthly hemispheric BBBD by intrarterial infusion of 1.4 M mannitol before receiving intrarterial methotrexate were tested. Blood samples (29 total) were obtained at four times for each hemispheric disruption: after anesthesia induction, 45 seconds after mannitol infusion, approximately 45 seconds after methotrexate infusion, and during recovery in the neurointensive care unit (4–5 hours after the procedure). The patients we chose had a very good BBB opening with mannitol infusion as confirmed by CT scans performed after the procedure was completed.

Figure 2:
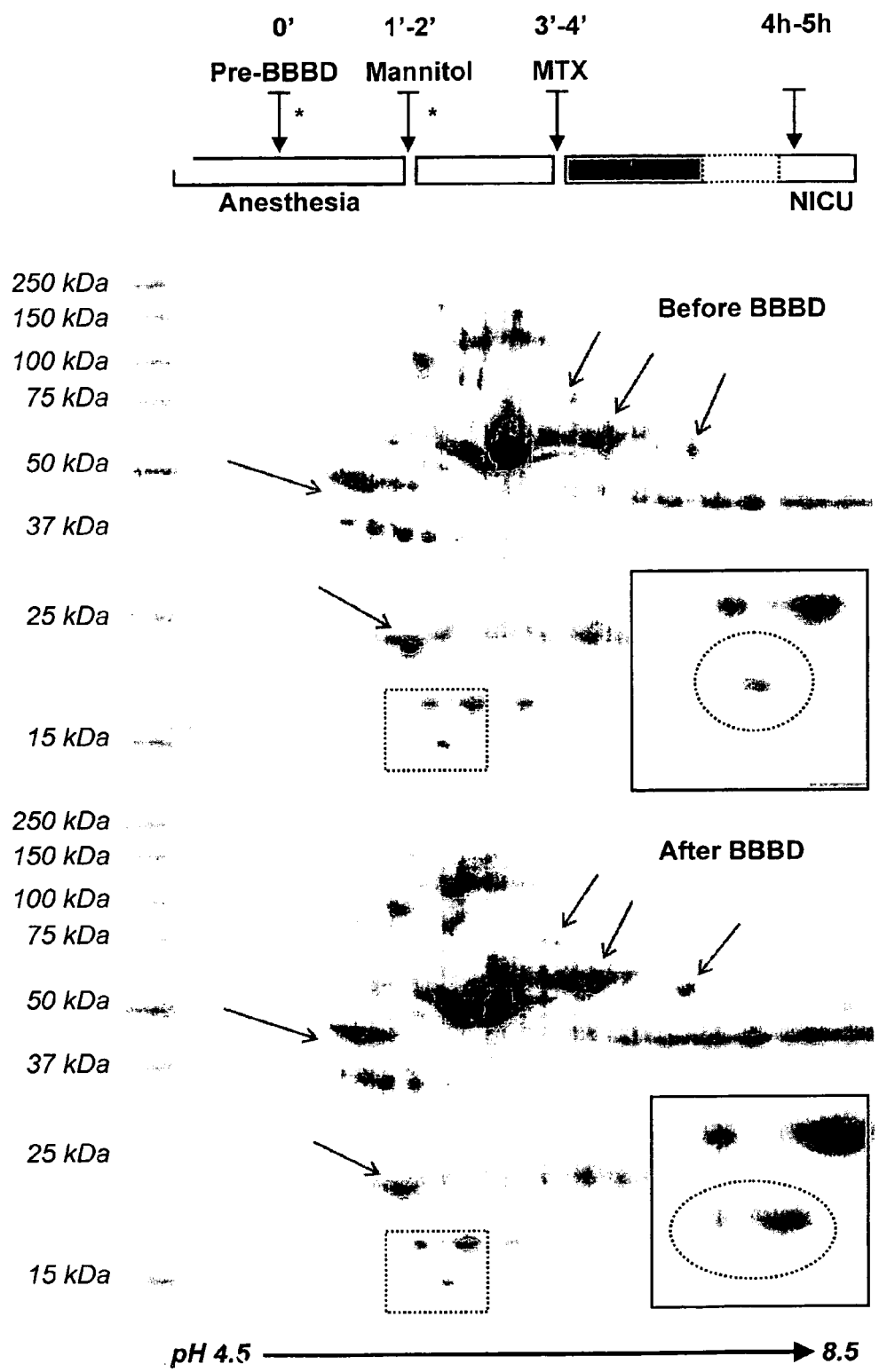
FIG. 2 is a 2D gel electrophonesis of human blood illustrating the detection of penetrating BBB markers.

Two-dimensional ("2-D") electrophoresis was used to compare human serum samples obtained from BBBD protocols to detect changes in protein content before and after opening the blood-brain barrier. FIG. 2 shows the results of a typical experiment. Care was taken to ensure that an equal amount of protein was loaded on each gel. A quantitative analysis was performed to confirm that gels prepared with pre-BBBD and post-BBBD were comparable. To this end, a comparison spot corresponding to haptoglobin (18 kDa, pI 5.4–6), was used as internal control.

Comparison of gels prepared with pre-BBBD and post-BBBD was achieved by use of automated computer software. A number of strategies were used to ensure that the changes in protein levels were caused by BBB opening and not random fluctuations. First, we considered significant only the appearance of detectable spots ex novo and excluded increased levels of pre-existing proteins. This criterion was used to minimize the possibility of uneven loading of gels as cause for the observed changes. Second, we excluded from further analysis changes that were not consistently observed in all BBBD. Thus, only spots that consistently appeared in post-BBBD gels in all three patients were further analyzed. Finally, we were limited to the identification of proteins that were amenable for mass-spectroscopy analysis on Coomassie-stained gels.

Figure 3:
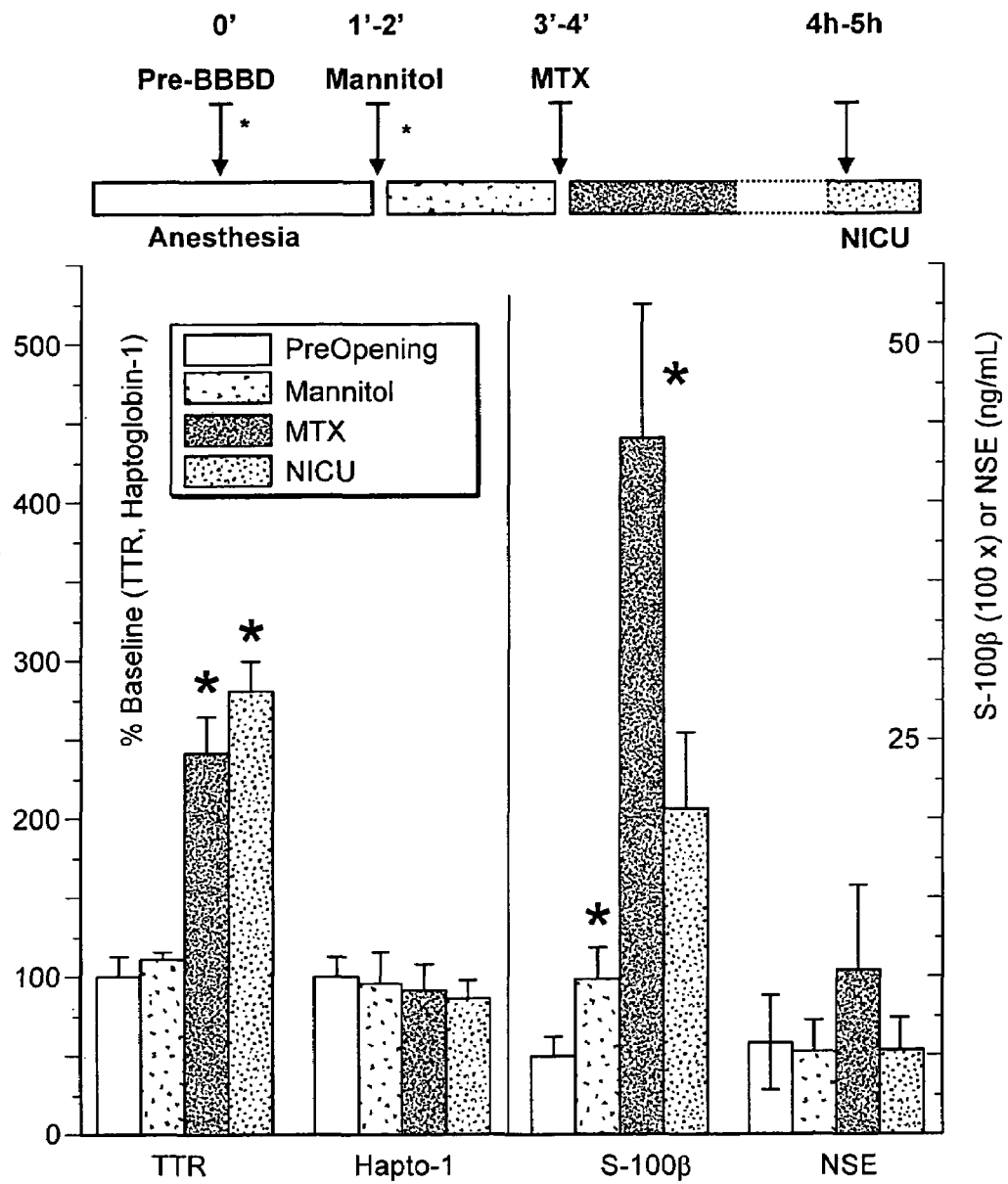
FIG. 3 illustrates a time course of serum protein changes after BBB disruption.

A 14 kDa and 5.5 pI protein appeared following all BBBD procedures. FIG. 2 illustrates detection of putative BBB markers by 2D gel electrophoresis of human blood proteins before and after osmotic opening of the BBB by intra-arterial mannitol. The samples used for loading were taken before mannitol injection and after chemotherapy. The time of the injection of the osmotic agent and the introduction of the chemotherapic agent (methotrexate) are shown in the timeline. Protein signals that remained unchanged are indicated by arrows. The region in which significant changes were observed is boxed by a dashed line. Note the appearance of a distinct spot after BBB disruption. This spot corresponded to a protein of approximate molecular weight of 14 kDa and a pI of 5.5. The size of the Coomassie-stained spot was quantified by proteomic software. FIG. 3 illustrates time course of serum protein changes after BBB disruption. S-100β, TTR, haptoglobin, and NSE were measured at the time indicated by the inset. Note that S-100β and TTR increased significantly after BBB opening but with different kinetics. NSE and haptoglobin-1 (Hapto-1) remained unchanged throughout the procedure. The mean±5D of three experiments is shown; $*p<0.05$. Note that the values for TTR and haptoglobin-1 are expressed as percentage change of spot intensity, whereas NSE and S-100β were measured by immunodetection techniques, and the values are expressed in nannograms per milliliter. The values for S-100β were scaled for clarity (100×). The asterisks indicate the actual time points at which the samples used for the gels shown were taken. This protein was subsequently identified as transthyretin. Previous results demonstrated that opening of the BBB by osmotic means causes a reproducible increase in serum levels of S-100β. In contrast, levels of the putative marker of neuronal damage, neuron-specific enolase (NSE) remained unchanged. The time-dependent appearance of TTR was compared with changes of NSE and S-100β during the same procedures. As shown in FIG. 3, BBBD caused S-100β and TTR changes characterized by distinct time dependency, whereas the internal controls haptoglobin and NSE remained essentially unaffected, on average. Note, however, that while S-100β increased significantly immediately (40 seconds) after mannitol injection and BBB disruption, TTR levels were elevated only after a longer delay.

After obtaining quantitative results describing protein changes, the qualitative nature of the low molecular weight protein shown in FIG. 2 was investigated. Protein identification was carried out by LC-MS microelectrospry MS. The region of interest was cut out from the gel and digested overnight with trypsin. The digest was analyzed by mass spectroscopy to determine peptide molecular weight and amino acid sequence. An additional spot (haptoglobin) was also processed to standardize the procedure for each individual gel.

All of the fragments matched perfectly with the sequence of human transthyretin, formerly known as pre-albumin (NBCI #4507225). In addition, the molecular weight and isoelectric point, of the spot identified in FIG. 2 corresponded to the monomeric form of TTR. Transthyretin is the major protein product of the choroids plexuses and represents 20% of total amount of protein in CSF. In plasma, TTR is present in a homotetrameric form with specific binding to several other proteins. $TTR_{CSF}$ is predominantly represented as a monomer, with accumulation of the tetrameric protein in epithelial cells of the choroid plexus.

Figure 4:
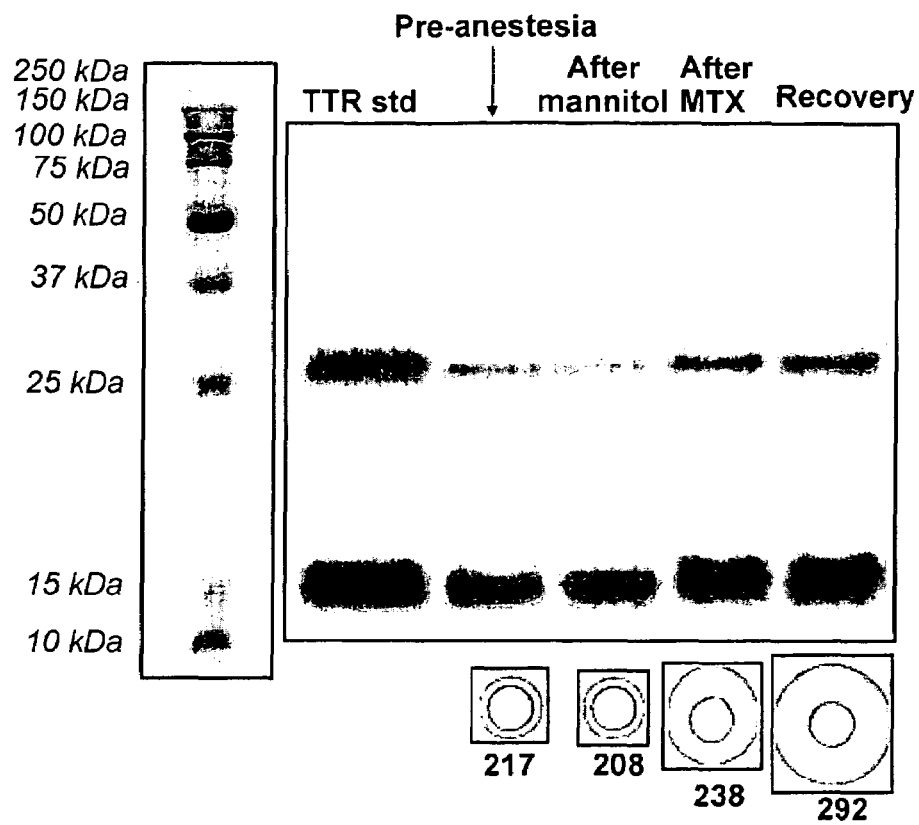
FIG. 4 illustrates the immunological of protein changes induced by BBB disruption.

In order to confirm that the protein spot identified by the BBBD procedure was indeed human transthyretin, we performed Western blot analysis on samples taken from the same patients utilized for 2-D gel electrophoresis. FIG. 4 illustrates immunological analysis of protein changes induced by BBB disruption. Top panel, denatured proteins were run in parallel with purified TTR (left lane). Western blot analysis revealed a significant increase of immunosignal for both low molecular weight isoforms. Quantitative analysis was performed on the same samples by RID (bottom panels); note the progressive increase of the immunoprecipitation signal surrounding the sample port (see Materials and Methods for details). The numeric values represent TTR levels extrapolated from these measurements and are expressed as micrograms per milliliter. Samples processed under denaturing condition displayed increased TTR immunoreactivity consistent with increased monomeric and dimeric TTR levels after BBBD. A commercially available TTR tetramer (55 kDa) was used as reference and loaded in the gel after processing under identical conditions. After denaturation, both dimeric and monomeric bands were identified by comparison with molecular weight standards. Furthermore, we used an alternative immunodetection approach based on quantitative radial immuno-diffusion (RID) of the sample in a gel containing antibody TTR. This test was in contrast performed on non denatured protein. However the observed increase in TTR as detected by RID does not necessary imply that the monomeric form of TTR was indeed increased in plasma.

Figure 5:
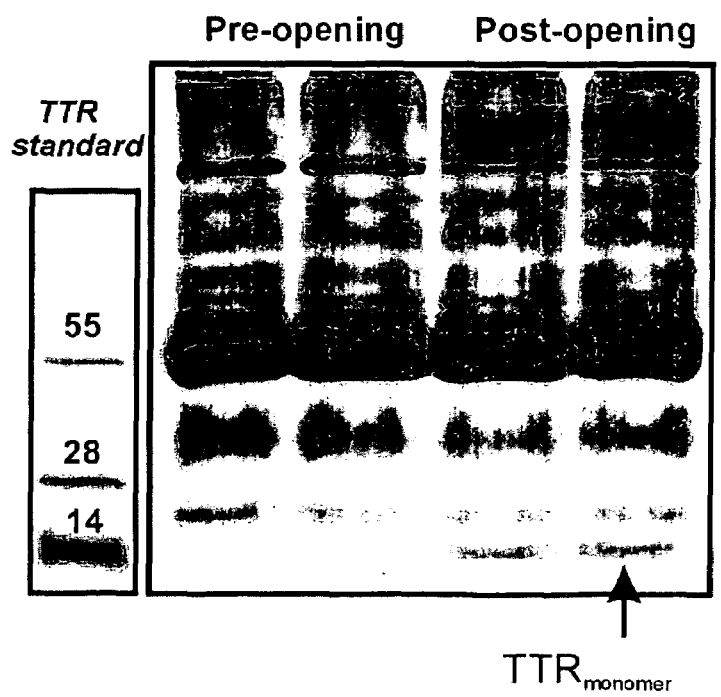
FIG. 5 illustrates non-SDS separation of pre-BBBD and post-BBBD samples.

Since the tests described above were either performed under conditions that do not allow preservation of native protein structure (e.g., monomer vs. tetramer) or by RID, we performed additional experiments on non-denatured proteins obtained from identical samples and separated by their molecular weight. FIG. 5 illustrates non-SDS separation of pre-BBBD and post-BBBD samples. Low molecular weight proteins obtained after separation with a sucrose gradient (cutoff 50 kDa) were loaded on a non-denaturating gel. Note the appearance of at 15 kDa molecular weight band after BBB disruption. Also note that this band corresponds to the monomeric form of standard TTR loaded on a separate gel. Purified TTR was again loaded as reference. Note that even under non denatured conditions a sharp increase in a band consistent with the monomeric form of TTR occurred after BBB disruption. Also note that this band was virtually absent prior the BBBD, confirming that the monomeric form of TTR is present predominately in the CSF.

The present invention allows detection of novel serum markers indicative of breaching of the cellular barriers that normally shield the brain from systemic influences. Transthyretin, particularly the monomeric form of transthyretin is a new marker of barrier integrity and affords proteomic strategies with clinical procedures where the BBB is disrupted to allow penetration of chemotherapic agents to treat brain tumors. Both mass spectroscopy and immunoblotting confirmed that TTR is increased early (minutes) after BBB disruption. However, the time course of TTR extravasation from CSF to plasma lagged behind that of another BBB marker, S-100β. In addition, monomeric TTR is normally present in high concentration in the CSF. These observations suggested that the appearance of TTR in serum after BBBD may preferentially indicate compromise of the blood-CSF barrier.

The original discovery of the usefulness of S-100β as indicator of BBBD was obtained by immunodetection methods and has led to a reinterpretation of the significance of serum S-100β in various pathologic scenarios. Indeed, while S-100β extravasation in blood was originally believed to represent brain damage, the finding that S-100β may increase in the virtual absence of, or preceding neuroglial damage prompted us to hypothesize that CSF protein appearance in serum may represent BBB disruption rather than brain damage. This was further supported by data demonstrating that large increases in S-100$\beta_{CSF}$ do not lead to significant plasma changes when the BBB is intact. However, S-100β increases in serum may also reflect peripheral neoplasms (e.g., melanoma or schwannoma), or other conditions where the BBB may be intact and neuronal damage absent. A broad proteomic analysis strategy was utilized to reveal other peripheral markers of BBB (dys) function.

Plasma electrophoresis has been used to diagnose human diseases. Conversely, CSF protein analysis has been instrumental in understanding CNS disorders. In particular, the presence of abnormal levels of plasma protein in CSF has been interpreted as sign of BBB failure. The same interpretation may be applied to modern contrast agent-based radiological investigations, where variously labeled plasma proteins are detected in the CNS when the BBB is breached. We demonstrated the feasibility and usefulness of the proteomic approach to screen blood for potential markers of BBB function. This was made possible by the availability of blood samples obtained from patients undergoing controlled and quantifiable (by CT) opening of the BBB by osmotic challenge. The same BBBD procedure was previously used to validate the role of S-100β to detect BBB opening.

The present invention allows for a substantially non-invasive determination of blood brain barrier permeability by peripheral detection of TTR. Due to its localization in the cerebrospinal fluid, TTR may, in addition to detect blood-brain barrier opening also correlate with failure of the blood-to-cerebrospinal fluid barrier or be independent of the blood-brain barrier opening. It is expected that TTR will be released very close in time to the opening of the blood brain barrier but that its appearance will lag behind that of other markers present in the extravascular space (S-100β). Thus upon detection of TTR, other markers of brain damage may be utilized to determine the onset of neuronal distress or damage. TTR and S-100β may be used to quantify the extent of blood-brain barrier damage and to confirm or rule out opening of the blood-to-cerebrospinal fluid interface.

One particular useful aspect of the present invention is in chronic neurological disease. In chronic neurological diseases, where the BBB opens before the disease becomes, pathology, becomes apparent. An example may be Alzheimer's disease, multiple sclerosis, or other diseases where it is believed that the BBB opens before the symptoms occur. In these cases, it would be expected that TTR would be elevated in the plasma before markers of neuronal damage become elevated. If routine measurements or samples are taken, a peripheral increase in TTR should precede an increase in the other markers.

The present invention encompasses a method for diagnosis and prognosis of a subject's BBB, comprising: contacting a serum sample derived from a subject with a sample containing TTR protein under conditions such that a specific antigen-antibody binding can occur; and detecting the presence of TTR present in the subject's serum, wherein the presence of immunospecific binding indicates level or degree to which the BBB is open.

In a specific embodiment of invention, the TTR protein is utilized to screen a subject's serum for the presence of TTR by means of sensitive and rapid immunoadsorbent assays or by other procedures. The present invention also provides for kits for carrying out the above described methods. The methods can be performed, for example, by utilizing pre-packaged diagnostic kits comprising at least a reagent for detecting TTR protein such as an anti-TTR antibody. Alternatively, the diagnostic kits may comprise an TTR peptide for detection of TTR autoantibodies in a subject derived sample.

In accordance with the invention, measurement of levels of TTR proteins in serum or body fluids can be used for the early diagnosis of diseases associated with an open BBB, such as neurological disorders. Moreover, the monitoring of TTR protein levels can be used prognostically to stage the progression of the disease and to evaluate the efficacy of compounds in penetrating the BBB.

The detection of TTR proteins in a body fluid from a subject can be accomplished by any of a number of methods. Preferred diagnostic methods for the detection of TTR proteins in the serum of a patient can involve, for example, immunoassays wherein TTR proteins are detected by their interaction with an TTR specific antibody. Antibodies useful in the present invention can be used to quantitatively or qualitatively detect the presence of TTR peptides. In addition, reagents other than antibodies, such as, for example, polypeptides that bind specifically to TTR proteins can be used in assays to detect the level of TTR protein expression.

Immunoassays to be used in the practice of the invention include but are not limited to assay systems using techniques such as Western blots, radioimmunoassays, ELISA (enzyme linked immunosorbent assay),"sandwich" immunoassays, immunoprecipitation assays, precipitation reactions, gel diffusion precipitation reactions, immunodiffusion assays, agglutination assays, complement fixation assays, immunoradiometric assays, fluorescent immunoassays, protein A immunoassays, to name but a few. Filtering of protein to isolate the monomeric form are necessary step prior to immunological detection by the aforementioned means.

In a preferred embodiment, a biological sample which may contain TTR proteins, such as serum or other biological fluids in which secreted proteins can localize, is obtained from a subject suspected of having a particular breach of the BBB or BCSFB a patient in which it is desirable to open the BBB. Immunoassays for detecting expression of TTR protein typically comprise contacting the biological sample, such as a serum sample derived from a subject, with an anti-TTR antibody under conditions such that specific antigen-antibody binding can occur, and detecting or measuring the amount of any immunospecific binding by the antibody. In a specific aspect, such binding of antibody, for example, can be used to detect the presence and increased expression of TTR proteins wherein the detection of increased expression of TTR proteins is an indication of a diseased condition. The levels of TTR protein in a serum sample are compared to norms established for normal individuals and for subjects at a variety of stages of BBB integrity or opening.

In an embodiment of the invention, the biological sample, such as a serum sample is brought in contact with a solid phase support or carrier, such as nitrocellulose, for the purpose of immobilizing any proteins present in the sample. The support is then washed with suitable buffers followed by treatment with detectably labeled TTR specific antibody. The solid phase support is then washed with the buffer a second time to remove unbound antibody. The amount of bound antibody on the solid support is then determined according to well known methods.

One of the ways in which TTR antibodies can be detectably labeled is by linking the antibody to an enzyme, such as for use in an enzyme immunoassay (EIA) (Voller, A., "The Enzyme Linked Immunosorbent Assay (ELISA)", 1978, Diagnostic Horizons 2: 1–7, Microbiological Associates Quarterly Publication, Walkersville, Md.; Voller, A., et al., 1978, J. Clin. Pathol. 31: 507–520; Butler, J. E., 1981, Meth. Enzymol. 73: 482–523). The enzyme which is bound to the antibody will react with an appropriate substrate, preferably a chromogenic substrate, in such a manner as to produce a chemical moiety that can be detected, for example, by spectrophotometric, fluorimetric, or by visual means. Enzymes that can be used to detectable label the antibody include, but are not limited to, horseradish peroxidase and alkaline phosphatase. The detection can also be accomplished by colorimetric methods that employ a chromogenic substrate for the enzyme.

Detection of TTR antibodies may also be accomplished using a variety of other methods. For example, by radioactively labeling the antibodies or antibody fragments, it is possible to detect TTR protein expression through the use of a radioimmunoassay (RIA) (see, for example, Weintraub, B., Principles of Radioimmunoassays, Seventh Training Course on Radioligand Assay Techniques, The Endocrine Society, March 1986). The radioactive isotope can be detected by such means as the use of a gamma counter or a scintillation counter or by autoradiography.

The antibody may also be labeled with a fluorescent compound. Among the most commonly used fluorescent labeling compounds are fluorescein isothiocyanate rhodamine, phycoerythrin and fluorescamine. Likewise, a bioluminescent compound may be used to label the TTR antibody. The presence of a bioluminescence protein is determined by detecting the presence of luminescence. Important bioluminescence compounds for purposes of labeling are luciferin, luciferase and aequorin.

Expression levels of TTR proteins in biological samples can be analyzed by two-dimensional gel electrophoresis. Methods of two-dimensional electrophoresis are known to those skilled in the art. Biological samples, such as serum samples, are loaded onto electrophoretic gels for isoelectric focusing separation in the first dimension which separates proteins based on charge. A number of first-dimension gel preparations may be utilized including tube gels for carrier ampholytes-based separations or gels strips for immobilized gradients based separations. After first-dimension separation, proteins are transferred onto the second dimension gel, following an equilibration procedure and separated using SDS PAGE which separates the proteins based on molecular weight. When comparing serum samples derived from different subjects, multiple gels are prepared from individual serum samples.

Following separation, the proteins are transferred from the two dimensional gels onto membranes commonly used for Western blotting. The techniques of Western blotting and subsequent visualization of proteins are also well known in the art (Sambrook et al, "Molecular Cloning, A Laboratory Manual", $2^{nd}$ Edition, Volume 3, 1989, Cold Spring Harbor). The standard procedures may be used, or the procedures may be modified as known in the art for identification of proteins of particular types, such as highly basic or acidic, or lipid soluble, etc. (See for example, Ausubel, et at., 1989, Current Protocols in Molecular Biology, Green Publishing Associates and Wiley Interscience, N.Y.). Antibodies that bind to the TTR proteins are utilized in an incubation step, as in the procedure of Western blot analysis. A second antibody specific for the first antibody is utilized in the procedure of Western blot analysis to visualize proteins that reacted with the first antibody.

The immunoassays can be conducted in a variety of ways. For example, one method to conduct such assays involves anchoring of TTR protein onto a solid support and detecting anti-TTR antibodies specifically bound thereto. The TTR proteins to be utilized in the assays of the invention can be prepared via recombinant DNA techniques well known in the art. For example, in instances where the nucleotide sequence of a DNA encoding an TTR protein is available, the DNA can be genetically engineered into an appropriate expression vector for large scale preparation of TTR protein.

It may be advantageous to engineer fusion proteins that can facilitate labeling, immobilization or detection of the TTR protein. See, for example, the techniques described in Sambrook et al., 1989, Molecular Cloning: A laboratory Manual, Cold Spring Harbor Press, Cold Spring Harbor, N.Y.

Alternatively, the TTR protein may be purified from natural sources, e.g., purified from cells, using protein separation techniques well known in the art. Such purification techniques may include, but are not limited to molecular sieve chromatography and/or ion exchange chromatography. In practice, microtitre plates are conveniently utilized as the solid support for the TTR proteins. The surfaces may be prepared in advance and stored.

Those skilled in the art will be able to determine optional assay conditions for each determination by employing routine experimentation.

In a first series of nonlimiting embodiments, a kit according to the invention comprises components for detecting and/or measuring human IgG antibodies directed toward TTR antigen. As one example, where the antibodies are detected and/or measured by enzyme linked immunoabsorbent assay (ELISA), such components may comprise target antigen, in the form of at least one and preferably a plurality of different TTR antigens or epitopes thereof, linked to a solid phase, and a means for detecting a human antibody bound to target antigen. Such means for detection may be, for example, an antibody directed toward the constant region of human IgG (e.g., rabbit anti-human IgG antibody), which may itself be detectably labeled (e.g., with a radioactive, fluorescent, colorimetric or enzyme label), or which may be detected by a labeled secondary antibody (e.g., goat anti-rabbit antibody).

In a second series of nonlimiting embodiments, a kit according to the invention may comprise components which detect and/or measure TTR antigens in the biological sample of a subject. For example, where TTR proteins are detected and/or measured by enzyme linked immunoabsorbent assay (ELISA), such components may comprise an antibody directed to epitopes of the TTR proteins which can be used to detect and/or quantitate the level of TTR expression in the biological sample. The antibody itself may be detectably labeled with a radioactive, flourescent, calorimetric or enzyme label. Alternatively, the kit may contain a labeled secondary antibody.

Further aspects of the invention provide methods as described above of monitoring the level of permeability of the BCSFB or the BBB. This is particularly useful when following a treatment course wherein the treatment course includes opening of the BBB. Compounds which typically have trouble passing through the blood brain barrier, where the compounds administered into the patient's bloodstream include, by way of non-limiting example, any of neuropharmacologic agents, neuroactive peptides (e.g., hormones, gastrointestinal peptides, angiotensin, sleep peptides, etc.), proteins (e.g, calcium binding proteins), enzymes (e.g., cholineacetyltransferase, glutamic acid decarboxylase, etc.), gene therapy agents, neuroprotective or growth factors, biogenic amines (e.g., dopamine, GABA), trophic factors to brain or spinal transplants, immunoreactive proteins (e.g, antibodies to neurons, myelin, antireceptor antibodies), receptor binding proteins (e.g., opiate receptors), radioactive agents (e.g., radioactive isotopes), antibodies, and cytotoxins, among others.

Related aspects of the invention provide methods for treating neurological disorders by monitoring the permeability of the compounds through the blood brain barrier in accord with the methods described above. Such disorders include tumors, cancer, degenerative disorders, sensory and motor abnormalities, seizure, infection, immunologic disorder, mental disorder, behavioral disorder, and localized CNS disease, among others.

In still further related aspects, the invention provides methods for modification of neurologic and neurologically-related activity (e.g., behavioral activity, memory-related activity, and sexual activity, among others) by such methods.

In still further related aspects, the invention provides methods for modification of neurologic and neurologically-related activity (e.g., behavioral activity, memory-related activity, and sexual activity, among others) by such methods.

All of the embodiments disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for diagnosing blood CSF barrier permeability in a subject comprising:
   obtaining a blood sample; and
   measuring a level of TTR protein in the blood sample, wherein elevated levels of TTR protein indicate blood CSF barrier permeability.

2. The method of claim 1, wherein the TTR protein is detected using an immunoassay.

3. The method of claim 1, further comprising:
   measuring a level of S-100β in said blood sample, wherein elevated levels of S-100β indicate blood brain barrier permeability in addition to blood CSF barrier permeability.

4. The method of claim 3, wherein said elevated levels of S-100β are selected from a first elevated level of S-100β, a second elevated level of S-100β and a combination of the first sad second elevated levels of S-100β, said first elevated level being associated with neuronal distress and the second elevated level being associated with brain damage.

5. The method of claim 1, further comprising:
   measuring the level of a marker of neuronal distress in said blood sample, wherein an elevated level of said marker indicates neuronal distress.

6. The method of claim 1, wherein said TTR is a monomeric form of TTR.

7. The method of claim 1, wherein said blood sample is selected from plasma, serum, and combinations thereof.

8. The method of claim 5, wherein said marker is selected from S-100β, NSE, GFAP, albumin, $TTR_{tetramer}$ and combinations thereof.

9. The method of claim 1 further comprising:
   obtaining a second sample from the subject; and
   measuring a level of S-100β in said sample, wherein an elevated level of S-100β indicates blood brain barrier permeability.

10. The method of claim 9, wherein said second sample is selected from blood, plasma, serum, CSF or combinations thereof.

* * * * *

UNITED STATES PATENT AND TRADEMARK OFFICE
CERTIFICATE OF CORRECTION

| | | |
|---|---|---|
| PATENT NO. | : 7,144,708 B2 | Page 1 of 1 |
| APPLICATION NO. | : 10/462222 | |
| DATED | : December 5, 2006 | |
| INVENTOR(S) | : Damir Janigro and Nicola Marchi | |

It is certified that error appears in the above-identified patent and that said Letters Patent is hereby corrected as shown below:

Claim 4, column 16, line 41, delete "sad" and insert --and--

Signed and Sealed this

Twentieth Day of March, 2007

JON W. DUDAS
*Director of the United States Patent and Trademark Office*